ary Examiner—Samuel Scott
United States Patent [19]

Thorne et al.

[11] Patent Number: 4,678,752

[45] Date of Patent: Jul. 7, 1987

[54] AUTOMATIC RANDOM ACCESS ANALYZER

[75] Inventors: Gale H. Thorne, Bountiful; Charles V. Owen, Highland; Randall W. Smith, Sandy; Ruth D. Goldberg, Salt Lake City; Scott D. Miles, Orem; Michael J. Claus, Salt Lake City, all of Utah

[73] Assignee: Becton, Dickinson and Company, Franklin Lakes, N.J.

[21] Appl. No.: 799,238

[22] Filed: Nov. 18, 1985

[51] Int. Cl.$^4$ ............................................. C12M 1/34
[52] U.S. Cl. ...................................... 435/291; 422/65; 422/100
[58] Field of Search ................................ 422/63–67, 422/100, 102; 435/291

[56] References Cited

U.S. PATENT DOCUMENTS

| | | | |
|---|---|---|---|
| 3,582,285 | 6/1971 | Hamilton | 422/100 |
| 3,994,594 | 11/1976 | Sandrock et al. | 422/102 |
| 4,054,416 | 10/1977 | Puff | 422/64 |
| 4,058,367 | 11/1977 | Gilford | 422/63 |
| 4,113,436 | 9/1978 | Werder et al. | 422/65 |
| 4,265,855 | 5/1981 | Mandle et al. | 422/65 |
| 4,326,851 | 4/1982 | Bello et al. | 422/63 |
| 4,383,041 | 5/1983 | Kutsusawa | 422/65 |
| 4,595,562 | 6/1986 | Liston et al. | 422/63 |

*Primary Examiner*—Samuel Scott
*Assistant Examiner*—Noah Kamen
*Attorney, Agent, or Firm*—Richard J. Rodrick

[57] ABSTRACT

An automated analytical apparatus comprises an introduction station for receiving a plurality of reagent packages. Each package has a plurality of receptacles, at least one of which includes a sample liquid to be analyzed, and at least one of which includes a liquid reagent for forming a reaction mixture with the sample liquid. A liquid transfer station is included for transferring liquid contained in one or more receptacles of a reagent package into, out of or among different receptacles thereof, including the formation of the reaction mixture. A detector is provided for detecting a characteristic of the sample by analyzing the reaction mixture contained in one of the receptacles of a package. A storage area is included within the apparatus for storing a plurality of reagent packages. A shuttle system transports individual reagent packages in any order and in any direction between the introduction area, the liquid transfer station, the detector and the storage area.

37 Claims, 7 Drawing Figures

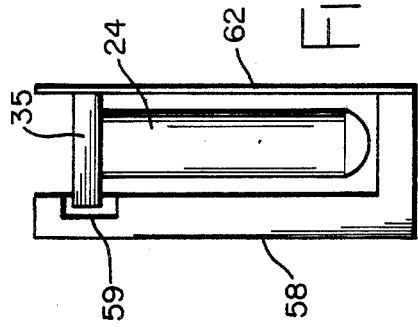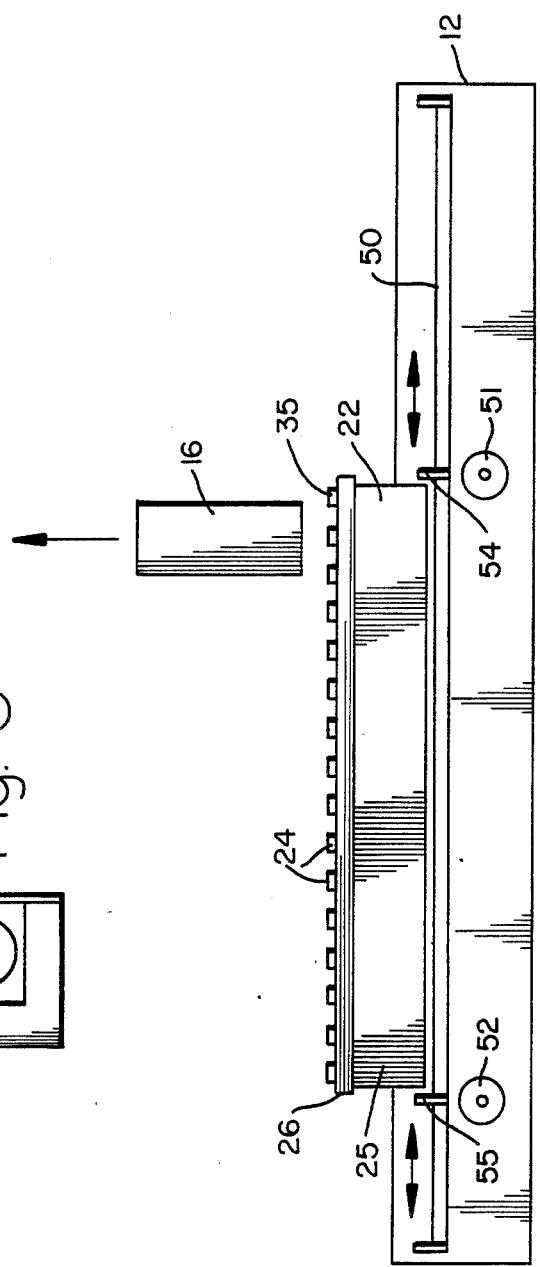

AUTOMATIC RANDOM ACCESS ANALYZER

BACKGROUND OF THE INVENTION

1. Field of the Invention.

The present invention relates to an automated analytical apparatus, and more particularly, concerns an automatic analyzer for the chemical or immunochemical testing of substances on a random access basis.

2. Description of the Prior Art.

There are many known and available analyzers for the chemical, immunochemical and/or biological testing of samples. In many instances, chemical tests are performed on biological fluids such as urine, blood serum, plasma, cerebrospinal fluid and the like. A sample of this fluid is typically combined with a prepared reagent liquid, and the resulting mixture, or subsequent mixtures, is analyzed by the apparatus for one or more characteristics of the sample. Reliance on automated clinical or chemical analyzers improves the efficiency of the laboratory procedures inasmuch as the technician typically has fewer tasks to perform than might be required if manual analysis were conducted. Moreover, automated clinical analyzers usually provide results much more rapidly, while also placing emphasis on accuracy and repeatability of the various tests.

A typical automated clinical analyzer available for many routine laboratory tests includes a transport or conveyor system designed to transport containers of sample liquids between various operating stations. Known conveyor systems or tracks travel in a circuit so that the containers with the sample liquids pass through the operating stations in sequential order. Thus, the sample liquid may pass through a reagent filling station, mixing station, reaction forming station, detection and analysis station, etc. One such automated clinical analyzer is described in U.S. Pat. No. 4,066,412, assigned to DuPont. In the DuPont system, however, the conveyor transports test packs for analysis in one direction only wherein the test packs, once inserted into the apparatus, must pass through without subsequent access before analysis occurs. In this regard, there is limited or minimal flexibility in the types of chemical tests which can be performed on an automated analyzer which relies on a sequential-station transport system.

In performing tests on various liquids, such as the biological liquids mentioned above, it is often desirable to test these samples after one or more reaction mixtures have taken place. For example, many automated analyzers rely on light or radiant energy to obtain information about the characteristics of the sample under analysis. Fluorescence, light scatter, absorption and other light-related parameters are detected and assessed with respect to the constituents of the sample under analysis. To place the sample in proper condition for such analysis, for example, surface preparation of cells to be immunofluorescently labeled, one or more reaction mixtures in reaction vessels might be necessary. Moreover, time may be required between different reaction mixtures so that sufficient incubation may occur for adequate preparation. For this type of testing in an automated analyzer, access to the sample liquid may be required a number of times after the sample has been placed into the apparatus. Thus, instead of loading the sample into the apparatus and obtaining sequential testing, such as in the apparatus described above, a storage vehicle might be required so that subsequent access to the sample liquid may be available. Such an instrument for access to the sample liquid or for subsequent reaction mixtures is sometime referred to as a random access analyzer. One such random access analyzer presently available is known as the TDX analyzer, sold by Abbott Laboratories, Chicago, Illinois. Random access analyzers also process different kinds of assays in any order.

Another feature which is common to presently available sequential and random access analyzers is the inclusion of the various reagents within the apparatus itself or placed near the apparatus for piping thereinto. Liquid reagents, in bulk form, are selected for the various types of tests which are to be performed on the sample liquids, and are stored in or near the apparatus. Reagent delivery units, such as pumps or the like, along with valves, control mechanisms and pipes are included in these automated analyzers so that different reagents may be mixed according to the type of test to be performed. A typical automated analyzer which includes the storage of bulk reagents is described in U.S. Pat. No. 4,483,927. Of course, as bulk reagents are stored or associated with the automated analyzer by pipes and pumping, the apparatus becomes more complex, particularly with respect to operation, maintenance and cost. Furthermore, the possibilities of error and miscalculation are increased due to the many and different reagents immediately available for forming different reaction mixtures in a single test.

The goal of automated random access analysis of samples, combined with an apparatus constructed in uncomplicated fashion, along with simplification of operator interface, still remains in the field of automated chemical analyzers. Previously described analyzers, and others which are presently known and available, have not completely satisfied the aforementioned goal. Even those automated analyzers which provide random access are still rather cumbersome or complicated, or include the storage of bulk reagents and attendant piping and valves for the different mixtures of liquids. The present invention is directed to achieving the goals set forth above.

SUMMARY OF THE INVENTION

The automated analytical apparatus of the present invention comprises means for receiving a plurality of reagent packages. Each package has a plurality of receptacles, at least one of which includes a sample liquid to be analyzed and at least one of which includes a liquid reagent for forming a reaction mixture with the sample liquid. Means are provided for transferring liquid contained in one or more receptacles of a reagent package to a different receptacle thereof, including the formation of the reaction mixture. Detector means are included for detecting a characteristic of the sample by analyzing the reaction mixture contained in one of the receptacles of a package. A plurality of reagent packages may be stored in storing means associated with the apparatus. Means are included for transporting individual reagent packages in any order and in any direction between the means for receiving, the means for transferring liquid, the detector means and the means for storing.

One embodiment of this aspect of the invention as described above further includes control means for regulating the order and direction of transport of individual reagent packages and for transferring the liquids from the receptacles of any one package to form the reaction mixture. Part of the control means includes a computer program into which information regarding the transportation of packages and the transfer of liquids is storable, retrievable, usable and/or changeable for analysis of the sample.

In a preferred embodiment of the present invention, an automated apparatus for analysis of samples comprises an introduction station for the placement of a rack containing a plurality of reagent packages. Each package has a plurality of receptacles at least one of which includes a sample liquid, and at least one of which includes a liquid reagent for forming a reaction mixture with the sample liquid. At a liquid transfer station liquid originally contained in one or more receptacles of a reagent package is transferred into, out of or among the different receptacles of the one reagent package so that the reaction mixture is formed. An incubation storage area is available for holding a plurality of reagent packages which have passed through the liquid transfer station. A shuttle system moves the rack so that each package therein is positionable adjacent the liquid transfer station. The shuttle system also removes one of the packages at a time from the rack and moves it into the transfer station and then into the incubation storage area. The shuttle system is further operable to move single packages from the storage area into the liquid transfer station and back into the rack in the introduction station. A detector, adjacent the storage area, is provided for analyzing the reaction mixture contained in one of the receptacles of any of the packages for determining one or more characteristics of the sample.

In accordance with the principles of the present invention, an automatic analyzer is provided for performing tests on samples. The apparatus of the present invention may be used for chemical, immunochemical, biological, and other analyses which lend themselves to automated procedures. Characteristics of the sample to be analyzed may be determined by a variety of different techniques, including photometry, nephelometry, spectrophotometry, fluorometry, chemiluminescence, bioluminescence, radiometry, enzyme analysis and the like. Inasmuch as the present invention is a random access automated analyzer, various samples may be tested irrespective of the sequence that those samples are introduced into the apparatus. Not only is the present apparatus more flexible in the type of tests which may be performed, but controls and computer programs are included which facilitate the random handling of the different operations of which the apparatus is capable. Automated control over the random handling of the various samples further simplifies the operator interface and reduces the activities of the technician responsible for conducting the tests.

Further, the apparatus of the present invention does not rely on the inclusion of bulk reagents for mixing various liquids for analysis. It is contemplated that the present invention will be used with a reagent package having one or more reagents pre-packaged therein. Different reagent packages will be previously prepared and available depending upon the type and nature of the analyses to be performed. In this regard, the apparatus of the present invention is expected to do nothing more than transfer specimen liquids to be sampled and previously-packaged reagent liquids among the different receptacles which form part of the unitized reagent package. The only bulk fluid which is expected to be included in the present apparatus is a rinsing reagent for cleaning and rinsing the liquid transfer elements which come in contact with the different liquids. Once again, as described above, operator interface is minimized since the present apparatus lends itself to computer programming. The transfer of liquids into, out of or among the different receptacles of a reagent package is performed automatically and in accordance with various assay templates, also covered by computer programming. By relying on pre-packaged reagents and sample liquids for testing, the present invention completely eliminates the complexities attendant to those apparatuses which rely on bulk reagents. Accordingly, the present invention further eliminates piping, valves and control mechanisms incorporated in those apparatuses which utilize bulk reagents. Complexities are therefore reduced, simplification is achieved, and costs are contained. In the operation of the present apparatus, simplification of construction and operation contributes to minimizing machine as well as operator errors, thereby improving the accuracy of the tests to be conducted. Other advantages and desirable features of the present invention will become apparent upon reading the detailed description which follows.

BRIEF DESCRIPTION OF THE DRAWINGS

FIG. 3 is a front elevational view schematically illustrating the shuttle system for incrementally moving the rack for positioning individual reagent packages at the liquid transfer station;

FIG. 5 is an end view of the reagent package as it appears in fixed position within the liquid transfer station;

DETAILED DESCRIPTION

Figure 1:
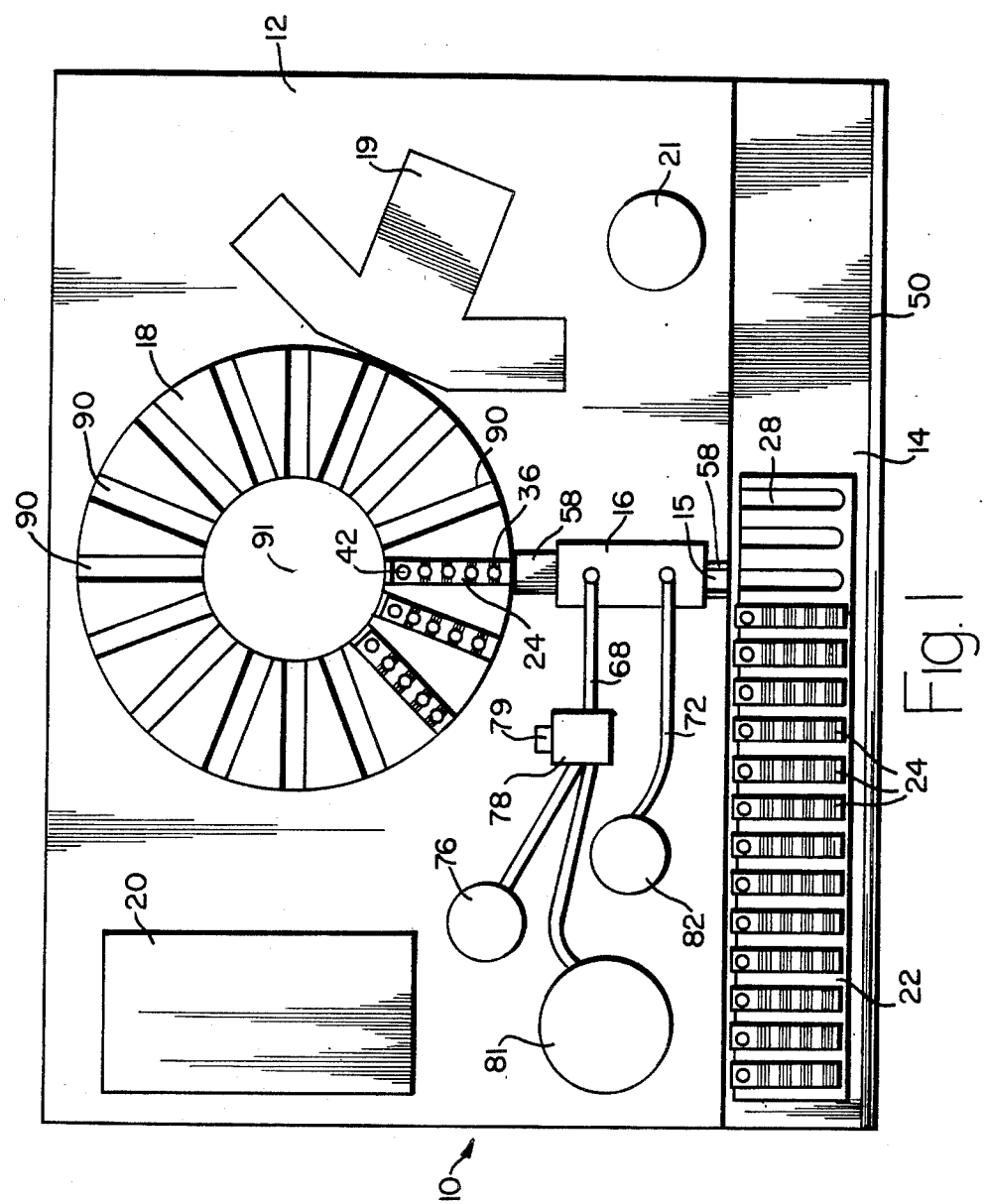
FIG. 1 is a top plan view schematically illustrating the major operative components of the preferred automatic random access analyzer of the present invention with the reagent package rack in position.

While this invention is satisfied by embodiments in many different forms, there is shown in the drawings and will herein be described in detail a preferred embodiment of the invention, with the understanding that the present disclosure is to be considered as exemplary of the principles of the invention and is not intended to limit the invention to the embodiment illustrated. The scope of the invention will be measured by the appended claims and their equivalents.

Adverting to the drawings, and FIG. 1 in particular, there is illustrated a schematic representation of the preferred embodiment of the automatic random access analyzer 10 of the present invention. Enclosing analyzer 10 is a cabinet 12 which holds the major components as illustrated in FIG. 1. These major components of the preferred automatic random access analyzer of the present invention are as follows: an introduction station 14, a shuttle system 15, a liquid transfer station 16, an incubation storage area 18, a detection assembly 19 and the electronics 20 for electrically operating the analyzer as will be described below. A fan 21 is typically included within cabinet 12 for cooling purposes and to permit the components to operate more efficiently.

Figure 2:
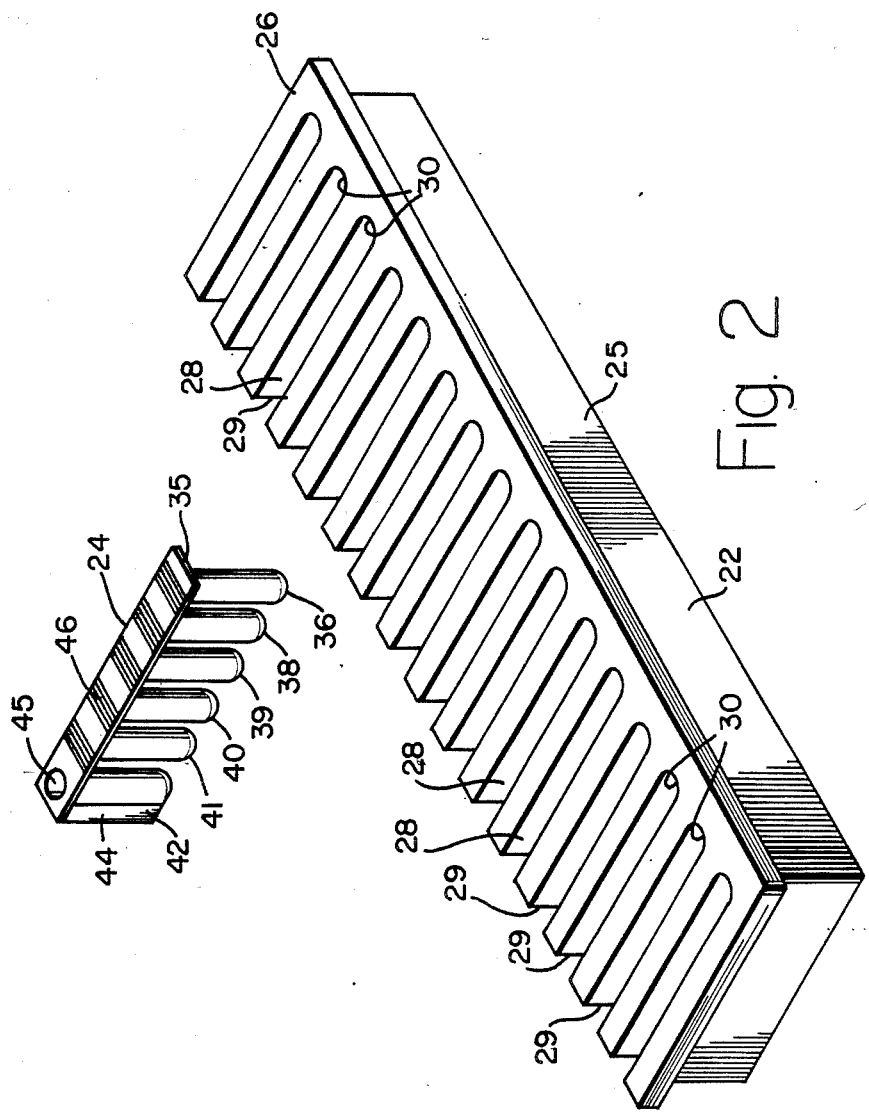
FIG. 2 is an enlarged perspective view of one configuration of a rack suitable for use with the present automatic random access analyzer, illustrating one embodiment of a reagent package with a plurality of receptacles and containing at least one pre-packaged liquid reagent.

Introduction station 14 and a rack 22 for holding a plurality of reagent packages 24 are illustrated in FIGS. 1–3. As mentioned above, the present invention does not contemplate storing reagents for the reaction mixtures in bulk containers within the apparatus. Instead, pre-packaged reagents are to be provided for analysis in one or more reagent packages 24. In order to present these reagent packages to the apparatus for subsequent analysis, introduction station 14 is designed to accept the placement of elongate rack 22 therein. As seen particularly in FIG. 2, rack 22 includes a base 25 and a top plate 26. A series of slots 28 is formed in rack 22, with the slots aligned in substantially parallel arrangement along the longitudinal axis of rack 22. Each slot preferably has an open 29 and a closed end 30 for facilitating the proper positioning of reagent package 24 therein. While sixteen slots are illustrated in the embodiment of FIG. 2, it is understood that the number of slots 28 may vary according to many factors, including available space, number of reagent packages being utilized, type of tests to be performed, etc.

Each reagent package 24 includes a substantially planar upper strip 35 and a plurality of receptacles 36,38,39,40,41 and 42. These receptacles are preferably aligned in a single row so that all of the receptacles, in a unitary package, may be slid or dropped into a slot 28. Strip 35 of the reagent package rests over the slot on top of plate member 26, thereby holding the reagent package in position in the rack. A square or rectangular wall 44 is preferably included at the end of reagent package 24 near end receptacle 42. Wall 44 serves as a keying feature so that receptacle 36 must be positioned within slot 28 so that it lies adjacent closed end 30. If the reagent package is inserted in the slot in the reverse orientation, however, the bar-code scanner (as described hereinafter) would signal an incorrect insertion.

For purposes of the present apparatus, receptacle 36 is expected to hold the final reaction mixture for analysis, so that its position in the rack is important as the reagent package is transported from station to station within the apparatus. On the other hand, receptacle 42 is expected to be the container into which the sample to be analyzed is originally placed. To that end, receptacle 42 is preferably left uncovered so that a sample liquid may be introduced through opening 45 into receptacle 42. The remaining receptacles are preferably covered and sealed insofar as one or more of the receptacles may include a pre-packaged liquid reagent therein. In the most preferred form, the cover for the remaining receptacles is a thin protective sheet 46 sealed over the open ends of the receptacles, except receptacle 42. Sheet 46 is fabricated so as to be readily pierceable by a sharp instrument, as will be described below. In addition, sheet 46 includes information thereon relating to the reagent package, for example, the assay type, expiration date, lot number, serial number, or other information. In the preferable form, this information on cover 46 is in the form of a bar-code which may be read electro-optically for obtaining the information thereon. The details of reagent package 24 are more completely described in a copending, commonly assigned patent application entitled, "A Self-Contained Reagent Package Device for an Assay," Ser. No. 740,593, filed on June 3, 1985, now U.S. Pat. No. 4,608,231.

Introduction station 14 preferably includes a platform 50 or the like for holding elongate rack 22. This platform is preferably placed at the front or forward part of cabinet 12 so that the rack loaded with reagent packages may be readily positioned in the apparatus by the laboratory technician. Platform 50 should be long enough to accommodate the movement of the rack from one side of the cabinet to the other so that each reagent package passes a position adjacent liquid transfer station 16.

Rack 22 is translationally moved in incremental steps in front of liquid transfer station 16 by means of shuttle system 15. Shuttle system 15 includes a drive mechanism or a conveyer represented by wheels 51 and 52 as seen in FIG. 3. Associated with these driving wheels are pins or tabs 54 and 55 which facilitate the incremental movement of rack 22 translationally across the introduction station.

Driving mechanisms 51 and 52 may move pins 54 and 55 in either direction so that rack 22 and its reagent packages 24 may be presented to liquid transfer station 16 in any order. Various position detectors may be included on shuttle system 15 to assure proper positioning of the rack and the reagent packages. Similarly, after analysis has been performed by the present apparatus, reagent packages 24 may be returned to the available slots in rack 22 merely be movement of the rack along the introduction platform to accept the used reagent packages.

Figure 4:
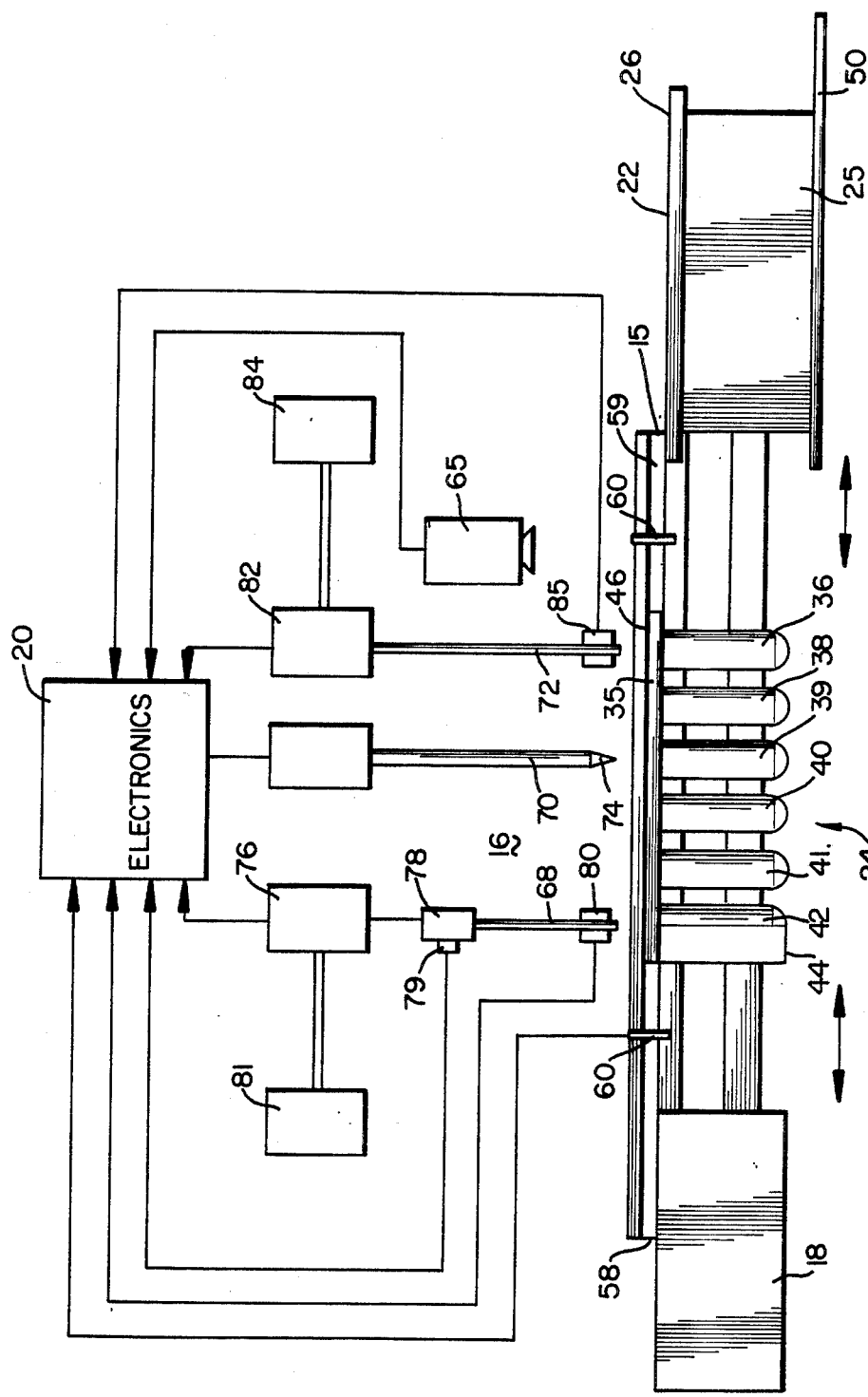
FIG. 4 is a side elevational view schematically illustrating the shuttle system for transporting a reagent package from the rack to the liquid transfer station and further schematically illustrating the elements of the liquid transfer station and bar-code scanner.

Referring now to FIG. 4, taken in conjunction with FIGS. 1 and 5, shuttle system 15 includes another drive mechanism for removing one of the reagent packages at a time from the rack and transporting it to liquid transfer station 16. To this end, a guide rail 58 is positioned so that it extends substantially perpendicular to the longitudinal axis of rack 24, and substantially parallel to slots 28 within the rack. Guide rail 58 includes a track 59 which is sized and shaped to accommodate strip member 35 of reagent package 24. One or more sliding tabs 60 are associated with track 59 and are movable therealong. Movable tabs 60 are adapted to engage strip member 35 of a reagent package positioned in a slot 28 of rack 22. Movement of tabs 60, and engagement with strip member 35, causes the reagent package to slide from the slot of the rack along track 59 until the reagent package enters liquid transfer station 16. It can be seen in FIG. 4 that guide rail 58 extends between rack 22 and the incubation storage area, represented by carousel 18. The shuttle system for transporting the reagent package is designed so that the reagent package may move in either direction between rack 22 and carousel 18, and also move back and forth within the liquid transfer station to different positions therein for access to the various receptacles of the reagent package.

Although not shown in FIG. 4 so as not to obscure the details thereof, liquid transfer station 16 includes a feature which is intended to fix the reagent package in position while in the liquid transfer station. As seen in FIG. 5, reagent package 24 is sandwiched between guide rail 58 and a resilient wall 62. This resilient wall may be in the form of a leaf spring or the like sufficient to impart an inwardly directed force against strip member 35 of the reagent package. Wall 62, however, is also sufficiently resilient so that the reagent package may slide along track 59 between guide rail 58 and wall 62. Once the reagent package stops at the liquid transfer station, wall 62, engaged against strip member 35, provides sufficient gripping action to maintain the position of the reagent package to prevent it from inadvertent sliding or movement. It is appreciated that techniques other than the spring-biased wall, as described in conjunction with FIG. 5, may be utilized for holding the reagent package in position to achieve the intended results.

FIG. 4 also illustrates the presence of a scanning device 65 which is positioned above the path that reagent package 24 slides along guide rail 58. Scanning device 65 is preferably an electrically operated bar-code scanner for reading the bar-code label as part of cover 46 of reagent package 24. Thus, as the reagent package is transported from rack 22 into liquid transfer station 16, the reagent package passes under bar-code scanner 65 and the information, as described above, contained on the bar-code label is electro-optically read thereby. Accordingly, all of the information contained on the reagent package label is electrically stored in the electronics 20 of the present random access analyzer. The position of bar-code scanner 65 between rack 22 and liquid transfer station 16 facilitates the obtaining of test-related information regarding a reagent package prior to disturbing the protective cover sealed on top of each reagent package.

In the normal analysis of sample liquids, it is preferred to group the various reagent packages into one or more sets. For example, the reagent packages may be grouped into calibrant singlets, calibrant duplicates, control singlets, control duplicates, unknown singlets and unknown duplicates. While bar-code label 46 on each reagent package 24 may provide full identification of the reagent package and related test information, the bar-code labels normally do not specify the set into which a specific reagent package should be grouped. Accordingly, instead of a reagent package containing liquid reagents and samples for analysis, rack 22 may include one or more marker packages which resemble a reagent package and are treated no differently by shuttle system 15 and bar-code scanner 65. Each marker package typically includes both machine-readable bar-code and human-readable information to specify reagent package sets, such as listed above.

For each set of reagent packages, there may be a specific marker package. When such markers are used, the laboratory technician normally places a marker package in a slot 28 of rack 22, followed by the reagent packages for that set. If more sets are to be placed in the rack, the technician separates the sets with appropriate marker packages. An empty slot or "end of set" marker package indicates that an "unknown" set follows. A marker package label read by bar-code scanner 65 informs electronics 20 that the current set has ended and a new set is ready for processing. If the first slot at the end of rack 22 does not contain a marker package, then, by default, the first set in the rack is classified as an "unknown." In the normal mode for the present invention, rack 22 is processed from right to left, as viewed in FIG. 1. With marker packages placed in rack 22, the technician merely places rack 22 into introduction station 14, designates normal or stat (immediate) processing, and the apparatus automatically commences the tests to be performed on the designated sets. Additional samples and marker packages may subsequently be added to available slots in the rack already placed in the instrument.

Liquid transfer station 16 includes a number of operative elements. These operative elements, a liquid transfer tube 68, a pointed punch 70 and a waste tube 72, are positioned above reagent package 24 and are preferably, but not necessarily, aligned in the arrangement as seen in FIG. 4. Insofar as reagent package 24 is movable, in either direction, along the guide rail within the liquid transfer station, the orientation of tubes 68 and 72 and punch 70 is normally not critical, and is left to the choice of the equipment manufacturer. However, some embodiments speed operation and enhance throughput.

As described above, all of the receptacles, except receptacle 42, of reagent package 24 are preferably covered by thin protective sheet 46. Receptacle 42 is normally left open so that the sample liquid may be introduced therein prior to loading the reagent package into the rack. One or more of the remaining covered receptacles of the reagent package may have liquid reagent therein. In order to gain access to the receptacles, punch 70 is operative to move rapidly downwardly to pierce cover 46 and expose the top openings of the receptacles. As will be described more completely hereinafter, the bar-code information on the reagent packages and the marker packages inform electronics 20 of the nature of the processing to be performed; accordingly, punch 70 is controlled by the electronics to punch through the openings of only those receptacles which need to be utilized for the specific assay to be performed. It is appreciated that reagent package 24 is programmed through the electronics to incrementally move, in either direction, so that any one of the receptacles is positioned under punch 70 so that the protective cover may be appropriately pierced. A sharp point 74 at the distal end of punch 70 facilitates this piercing action.

Once the open ends of the receptacles of reagent package 24 are exposed by means of punch 70, liquid is transferred into, out of or among the different receptacles of the regent package. Such liquid transfer is achieved by virtue of liquid transfer tube 68 associated with a dual-action pump 76. In one mode, pump 76 aspirates liquid from one or more of the receptacles of the reagent package. Liquid is withdrawn from any one or more of the receptacles through hollow tube 68, the lumen of which is in fluid communication with a reservoir 78. This reservoir is in the fluid path between tube 68 and pump 76 for the temporary storage of liquid aspirated from one or more of the receptacles. Insofar as reaction mixtures, including the reagent liquids, are preferably heated to an elevated temperature in incubation storage area 18, it is preferred to pre-heat the various liquids which form the liquid reaction mixtures. To this end, a heater 79 is provided to heat the liquid contents of its reservoir to an elevated temperature. For example, the small amounts of liquids which are aspirated into reservoir 78 may be rapidly heated to a suitable temperature, e.g., 37° C.

In the second mode of dual-action pump 76, liquid contained in reservoir 78 is pumped out of the reservoir and delivered into one or more receptacles of reagent package 24. This transfer of liquids from reservoir 78 into the different receptacles facilitates the mixing of the sample liquid and any liquid reagents originally included in one or more receptacles of the reagent package to thereby form one or more reaction mixtures for subsequent analysis.

In similar fashion as the movement of punch 70, tube 68 is operative to move up and down so that it travels into and out of any one of the receptacles of the reagent package. Electronics 20 are preprogrammed to regulate the movement of liquid transfer tube 68 depending upon the test information set forth on the bar-code labels and marker packages. An element which aids in the regulation of volume control may be a liquid level sensor 80 located at or near the distal end of liquid transfer tube 68. When tube 68 moves downwardly into one of the receptacles, sensor 80 is capable of detecting the upper level of liquid therein. Not only does sensor 80 contribute to precision in withdrawing and delivering liquids into or out of a receptacle, but this sensor helps to minimize the penetration of the distal end of tube 68 into the liquid. A minimal distance of travel of tube 68 into the liquid means that subsequent rinsing or cleaning of that tube will be easier. Also, control of the penetration of tube 68 into the liquid contributes to minimizing cross-contamination between the various receptacles into which tube 68 travels.

Rinsing liquid for cleansing reservoir 78, tube 68 and associated components, is included in a container 81. Rinsing reagent is pumped out of container 81 by virtue of pump 76 so that the rinsing liquid is available to cleanse the aforementioned elements, as well as one or more of the receptacles, if so desired.

Further included in liquid transfer station 16 is a second pump 82 which is operative to withdraw waste liquid from one or more of the receptacles of a reagent package. Hollow tube 72 has its lumen in fluid communication with withdrawal pump 82. Similar to tube 68, hollow tube 72 is pre-programmed to move downwardly into one or more of the receptacles for withdrawing waste liquids out of those receptacles and delivering the waste to a waste container 84. A liquid level sensor 85 may, if desired, be provided at the distal end of tube 72 for detecting the upper level of liquid in any one of the receptacles from which waste is to be withdrawn.

An example of the operative steps within the liquid transfer station with respect to a single reagent package will not be provided to assist in the understanding of the present invention. A reagent package, such as illustrated in FIG. 2, has a liquid specimen to be assayed deposited in empty receptacle 42 through open end 45. Assuming that blood serum is to be assayed for a determination of trace amounts of proteins, hormones, drugs or the like, the prepared serum is deposited into receptacle 42, and the reagent package positioned in the appropriate slot of the rack. Reagent package 24 is transported from rack 22 into liquid transfer station 16 and, within the liquid transfer station, the reagent package is incrementally stepped so that punch 70 pierces protective cover 46 and exposes the open ends of receptacles 36, 38, 39, 40 and 41, just before use. By virtue of the pre-programming, reagent package 24 is stepped so that receptacle 40, with diluent therein, comes directly under tube 68. A measured amount of the diluent is withdrawn from receptacle 40 by the action of pump 76. This measured amount of diluent is temporarily stored in reservoir 78. Next, the reagent package is incrementally moved so that receptacle 42 is positioned under tube 68. Prepared serum is withdrawn from receptacle 42, and the serum is also temporarily maintained within reservoir 78, where it may be heated. Receptacle 39, left empty in the original package, is then positioned so that it is directly under tube 68. The measured amount of serum and the diluent within reservoir are then pumped into empty receptacle 39. The reagent package is subsequently incremented so that receptacle 41 is positioned under tube 68. A tracer material is then withdrawn from receptacle 41 into reservoir 78. Next, a measured amount of the diluted specimen is withdrawn from receptacle 39 through tube 68 into reservoir 78. Receptacle 38 is then positioned under tube 68, whereupon the diluted specimen and tracer material from reservoir 78 are pumped into receptacle 38. There, the tracer material reacts with one or more components of the diluted serum. Radioactive, fluorescent and the like materials are typically used as tracers.

At this time an incubation step may be necessary to allow sufficient time for the tracer material to react with the components of the diluted serum. The reagent package with the reaction mixture as described above is then transported out of liquid transfer station 16 into incubation storage area, preferably represented by carousel 18. Guide rail 58 and track 59 extend to carousel 18 so that reagent package 24 may be deposited into one of the radially extending slots 90 therein. Slots 90 are similar in size and shape to slots 28 of rack 22, so that a reagent package may be maintained therein, and freely slide in and out when the need for transportation arises. It can be seen particularly be referring to FIG. 1 that reagent package 24 is positioned within slot 90 so that receptacle 42 is at the innermost position, whereas receptacle 36 is at the outermost position. It is in receptacle 36 that the reaction mixture is to be analyzed by detector assembly 19.

Carousel 18 is rotatable about a shaft 91 in both clockwise and counterclockwise directions. In this regard, each slot 90 is positionable with respect to guide rail 58 so that reagent packages may be randomly deposited into carousel 18 or randomly withdrawn therefrom for transportation into or through liquid transfer station 16. Although carousel 18 is illustrated in FIG. 1 as having an equal number of slots 90 as the number of slots 28 in rack 22, the numbers of respective slots may, however, differ. For instance, in one embodiment of the present invention, carousel 18 may contain at least twice the number of slots as there are slots in rack 22 for holding reagent packages. This number of slots in carousel 18 facilitates the handling of more than one rack at a time. One of these slots may be used as a detector calibrator slot.

It is the purpose of carousel 18 to store reagent packages which need to undergo incubation of the different reaction mixtures. Due to the complete random transportation into and out of carousel 18, different reagent packages may be incubated for different times. Accordingly, reagent packages need not, and most frequently are not, positioned in the carousel for sequential movement before detector assembly 19 for analysis. Positioning of the reagent packages before the detector assembly is also done on a random basis according to a preprogrammed schedule, the details of which will be described hereinafter.

Heating of the reagent packages within carousel 18 is preferably achieved by virtue of a temperature-controlled environment surrounding the carousel. Preferably, but not shown in the drawings, a separate compartment may be provided around carousel 18 with an air bath for maintaining temperature within the compartment at a relatively constant temperature.

Returning now to the example set forth above, the reagent package was transported into carousel 18 with a reaction mixture within receptacle 38. After sufficient incubation time in the carousel, the carousel is pre-programmed to rotate so that the slot containing this particular reagent package is aligned with the shuttle system. Reagent package 24 is then moved back into liquid transfer station 16 so that receptacle 38 is positioned under tube 68. A measured amount of the reacted mixture in receptacle 38 is withdrawn and temporarily stored in reservoir 78. Reagent package 24 is then incremented so that receptacle 36 is under tube 68. The measured amount of the reacted mixture temporarily held in reservoir 78 is then pumped into receptacle 36. A further reaction may take place in receptacle 36 or the previously reacted mixture may remain the same. Reagent package 24 is then transported back into carousel 18, whereupon further incubation may take place for a period of time, or the reagent package may be scheduled for analysis by detector assembly 19.

Insofar as the present invention is useful for analyzing samples in many different forms, detector assembly 19 may be provided in a variety of different configurations and functions. Many of these different types of analyses were mentioned above. One embodiment of the present invention includes a detector assembly 19 which uses the principle of light energy for conducting the analysis. For example, the reaction mixture in receptacle 38 may contain fluorescent markers associated with one or more of the components of the sample under investigation. A light source, such as an incandescent lamp, laser or the like, is provided in conjunction with detector assembly 19 to direct light energy into receptacle 36 containing the reaction mixture. As pointed out above, receptacle 36 is at the outermost end of slot 90 in carousel 18 so that receptacle 36 is presented in front of detector assembly 19. As light from detector assembly 19 shines through receptacle 36, the fluorescent markers in the mixture become excited, and a fluorescence emission occurs. Detection of this fluorescence by an appropriate fluorescence detector, such as a photomultiplier tube or the like, permits the determination of the quantity of a characteristic substance which is present in the sample under analysis. This type of detector assembly facilitates fluoroimmunoassays (FIA) and immunofluorometric assays (IFMA). Different detectors which measure light absorption may also be used in the apparatus. Of course, other assays may be carried out in the present invention, particularly with the use of light energy for conducting the analysis. For instance, nephelometry may be performed by changing the fluorescence detector to a light scatter detector within the detector assembly. It is appreciated that the type of detector assembly for use in the present invention may be selected so as to impart sufficient flexibility for many different types of assays compatible with the present invention.

Figure 6:
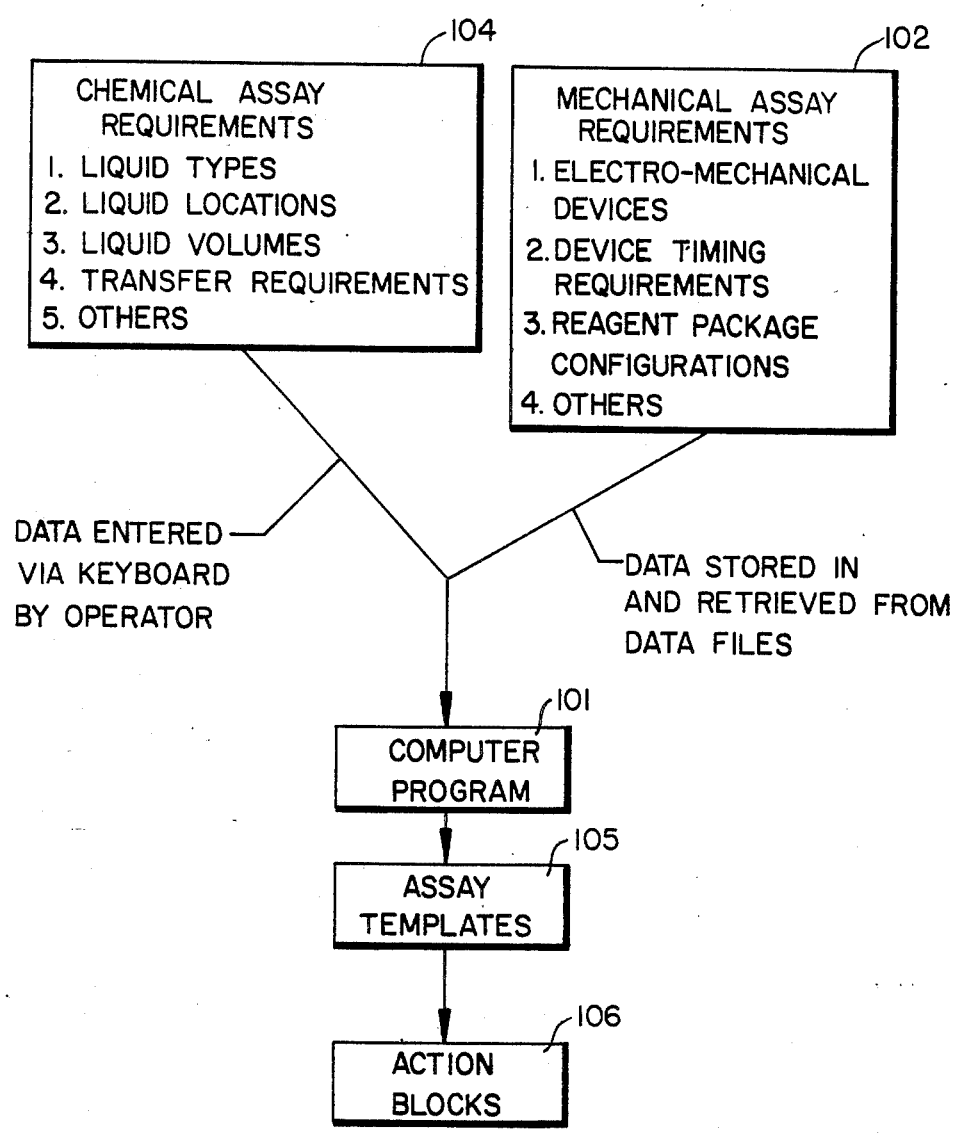
FIG. 6 is a block diagram of the assay formatting computer program for regulating the actions to be performed in the analyzer.

Regulation of some operative functions of the present automatic random access analyzer is controlled by a computer program 101 as illustrated in FIG. 6. This computer program and the associated computer functions are included in the electronics 20 of the apparatus. It is the purpose of computer program 101 to provide an interface into the apparatus through which it is possible to define the actions required to process a sample of any particular chemistry type. By virtue of this interface, assays may be formatted for regulating the actions of liquid transfer station 16 for transferring liquid into, out of or among the receptacles of reagent package 24. As a result of computer program 101 and the interface which it provides, the laboratory technician is free to concentrate on the biological and chemical components of the assay definition, since the apparatus automatically manages the mechanical and electrical functions for carrying out the assays.

As illustrated in FIG. 6, assay data is stored in data files of computer program 101, and may be subsequently retrieved for performing the tests. This stored data, identified by numeral 102, include the mechanical assay requirements such as the control of electromechanical devices, the timing requirements of those devices, reagent package configurations, and other such requirements. In addition to stored data, other data (calibration values, standard values, default control, etc.) may be entered via the keyboard (not shown) associated with the random access analyzer for interface with computer program 101. Data to be entered, designated by numeral 104, may include chemical assay requirements such as liquid types, liquid locations (i.e., different receptacles), liquid volumes, transfer requirements and the like. It is also feasible to employ a button or switch as a "GO" control for either STAT or normal operation.

When the present random access analyzer receives a reagent package including a liquid sample of any particular chemistry type, the bar-code label information is read and fed to the electronics for processing by computer program 101. By retrieving stored data 102 and relying upon STAT or normal data 104, a determination is made as to what actions need to be performed to properly process the liquid sample. This procedure includes the examination of one or more assay templates 105, each of which contains a list of action blocks 106. To process a liquid sample of any particular chemistry, the analyzer performs the actions indicated by each action block in the corresponding assay template. It is preferable to commence the first action in each action block after an indicated incubation period, if any, has passed subsequent to completion of the previous action block. Along these lines, it is also preferable to separate each pair of action blocks in an assay template by an incubation time. Action blocks 106 include a list of actions to be performed by the analyzer along with the time that each action is to begin. In addition, multiple assay templates may specify the same action block. For example, since it is contemplated that all, or most, of the reagent packages would have one of its receptacles analyzed by detector assembly 19, most of the assay templates specify the same final action block, i.e., the detection block.

Other action blocks include the movement of each reagent package into the different positions within the liquid transfer station, the movement of the package into and out of the carousel, positioning of a reagent package adjacent the detector assembly, and transportation of a reagent package back into the rack after the analysis has been completed. Assay templates 105 and action blocks 106 also control the various transfers of liquids into, out of and among the receptacles of a reagent package, in accordance with chemical assay requirements 104 for the analysis of a sample of a particular chemistry type.

Figure 7:
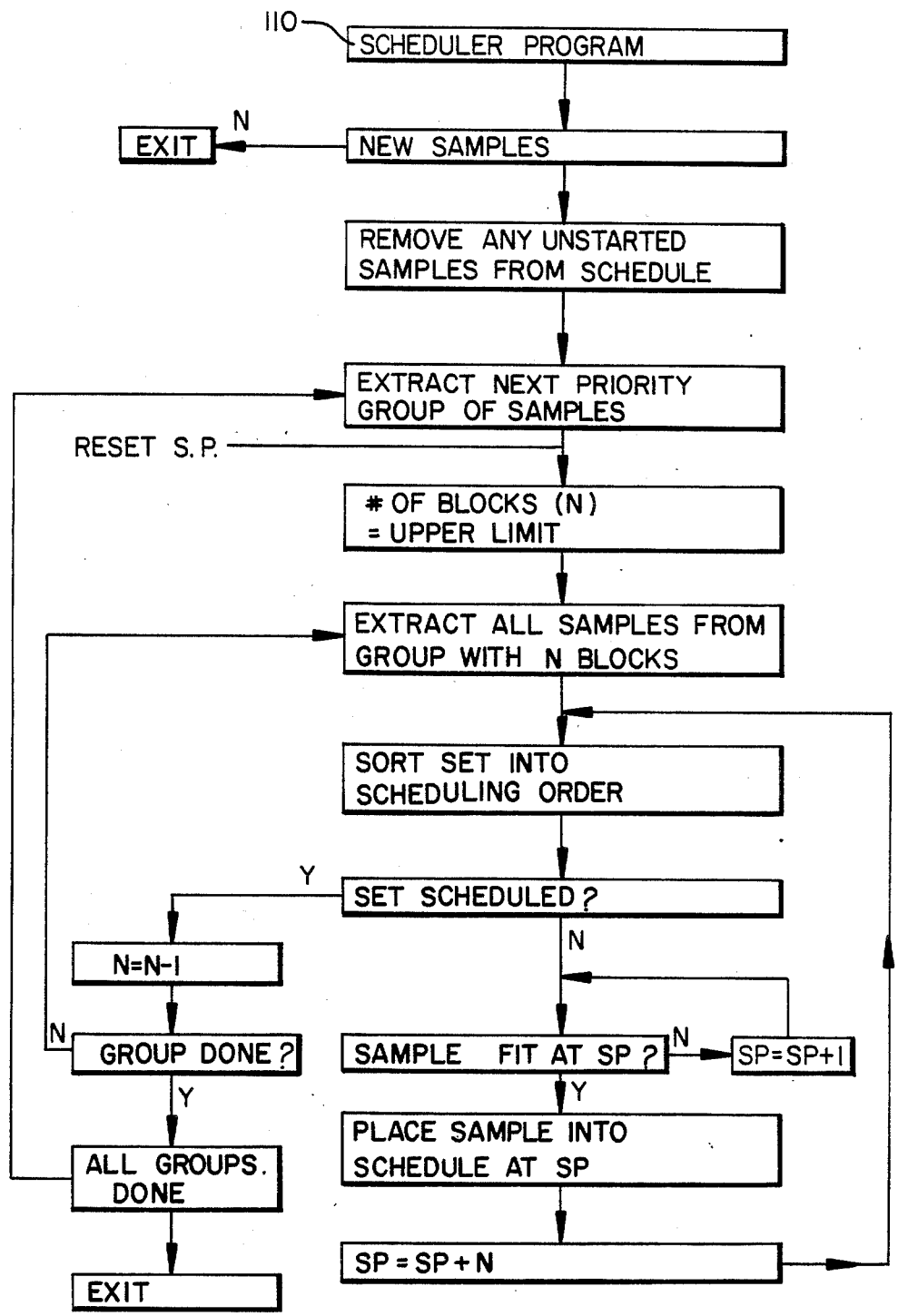
FIG. 7 is a flow chart of the scheduler computer program for determining the sequence that reagent packages pass to or through the different operating stations within the present automatic random access analyzer.

Included in the present automatic random access analyzer is another computer program, or a subroutine of program 101, associated with electronics 20 and the operative elements of the analyzer, for scheduling the sequence of events carried out by the analyzer. FIG. 7 represents one embodiment of a flow chart of a scheduler program 110 for determining the sequence that reagent packages pass, in any order and in any direction, between the rack, the liquid transfer station, the incubation storage area and the detector assembly within the present automatic random access analyzer. Scheduler program 110 is responsible for examining all of the actions required to complete the processing of the samples which are currently in the apparatus, and arranging them into a sequence which attempts to use the capabilities of the apparatus in an efficient manner. To achieve such an orderly arrangement, the scheduler is programmed to regulate the movements of different reagent packages to and from the various stations of the analyzer.

As the first step of the scheduler program, an examination is made to determine whether there are reagent packages, having samples to be analyzed, presently positioned in the apparatus and which need to be scheduled. If there are no new reagent packages in the apparatus, the scheduler takes no action. When new reagent packages are detected, the following actions are taken in accordance with the preferred scheduling format:

a. all the reagent packages in the current schedule on which no actions have started are recognized along with new reagent packages in the apparatus;
   b. the total number of reagent packages which need to be scheduled are then identified; and
   c. the identified reagent packages are scheduled.

In accordance with the preferred embodiment of the present invention, reagent packages are scheduled with the following priorities:

a. no analyses of samples in stored reagent packages presently underway are to be aborted; processing for reagent packages which already have been started is continued in interrupted fashion;
   b. Stat (immediate) samples in reagent packages are scheduled before all other samples; and
   c. reagent packages which have been in the apparatus for longer than a certain length of time are scheduled before reagent packages which recently have been added.

Each of these priority groups of samples in reagent packages is extracted, by the computer program, from the total number of samples to be scheduled. Within each group, the more complex samples are placed into the schedule prior to the simpler samples. Complexity is preferably determined by the number of processing or action blocks (such as action blocks 106 described in conjuction with FIG. 6) required to process the sample. For instance, samples with multiple action blocks are scheduled prior to the simpler one or two action block assays. Scheduler 110 extracts all of the samples from the group that have exactly N action blocks associated with them, with N set to the maximum number of blocks that may occur, as seen in FIG. 7. A resulting list of samples is designated as a schedule plan. The schedule plan is placed into the schedule, N is decremented by one, and the process is repeated until all of the samples in a priority group have been placed in the schedule.

To perform the scheduling of a schedule plan, the plan is first sorted into scheduling order. Within a plan, the reagent packages with samples having shorter incubation periods are scheduled prior to samples having longer incubation periods. Samples are sorted into the scheduling order, and placed into the schedule one at a time until all the samples in the plan are scheduled. For placement of a sample into the schedule, scheduler 110 makes use of an expedient referred to as a schedule pointer. This pointer contains the number of the time block at which the first process block of the sample should be started. The schedule pointer is reset to point to the first free time block in the schedule at the start of each priority group. In scheduling a single sample, scheduler 110 attempts to fit the sample into the schedule at the point indicated by the schedule pointer. If the sample does not fit at that point, the schedule pointer is incremented by one. This process is repeated until the sample fits into the schedule. After fitting the sample into the schedule, the schedule pointer is incremented by N, representing the number of action blocks in the most recently scheduled sample. When all samples have been scheduled, the functions of scheduler program 110 are completed. The time interval between successive executions of scheduler program 110 may be preset or may be varied according to choice of the operator depending upon the tests to be conducted.

Thus, the present invention provides an automated analytical apparatus for the analysis of samples on a totally random access basis. The present invention provides a laboratory technician with considerable flexibility in conducting analyses of samples of different chemistry types. Random access and regulation of the reagent packages of the present invention are handled on an automated basis with particular reliance on computer interface for minimizing manual activities. Since the samples to be analyzed by the present analyzer are included in an self-contained reagent package, construction of the present apparatus is greatly simplified inasmuch as bulk liquid reagents are not required as in presently available clinical analyzers.

What is claimed is:

1. An automated apparatus for analysis of samples comprising:

an introduction station for the placement of a rack containing a plurality of reagent packages, each package having a plurality of receptacles at least one of which includes a sample liquid, and at least one of which includes a liquid reagent for forming a reaction mixture with said sample liquid, said introduction station including a platform for holding an elongate rack having a plurality of slots aligned in substantially parallel arrangement along the longitudinal axis of said rack, said reagent packages being removably positioned in said slots;

a liquid transfer station for the transfer of liquid contained in one or more receptacles of a reagent package among the different receptacles of said one reagent package so that a reaction mixture may be formed;

an incubation storage area for holding a plurality of reagent packages which have passed through said liquid transfer station;

a shuttle system for moving said rack so that each package therein is positionable adjacent said liquid transfer station and for removing one of said packages at a time from the rack and moving it into said transfer station and into said incubation storage area, said shuttle system being further operative to move individual packages from the storage area into said transfer station and into said rack in the introduction station; and a detector for analyzing the reaction mixture contained in one of the receptacles of any of said packages for determining a characteristic of the sample.

2. The apparatus of claim 1 wherein said liquid transfer station includes a dual-action pump for aspirating liquid from one or more receptacles of a single reagent package and for delivering said aspirated liquid into one or more receptacles of said reagent package, whereby said transfer of liquids includes the mixing of said sample liquid and said liquid reagent to form a reaction mixture in at least one of the receptacles of said package.

3. The apparatus of claim 2 wherein said liquid transfer station includes a hollow tube having its lumen in fluid communication with said pump, said tube being operatively mounted in said liquid transfer station to move into and out of the receptacles of the package for the transfer of liquids.

4. The apparatus of claim 3 wherein said liquid transfer station further includes a reservoir in the fluid path between said tube and said pump for the temporary storage of liquid aspirated from one or more of said receptacles.

5. The apparatus of claim 4 wherein said liquid transfer station further includes a heater for heating the liquid in said reservoir.

6. The appparatus of claim 3 wherein said tube includes a liquid level sensor for sensing the level of liquid in any of the receptacles into which the tube is moved.

7. The apparatus of claim 3 wherein said liquid transfer station includes an operative punch member having a sharp point at its distal end for piercing a thin protective cover sealed over open ends of one or more receptacles of the reagent package to thereby gain entry into such receptacles.

8. The apparatus of claim 4 wherein said liquid transfer station further comprises rinsing means in fluid communication with said tube and said reservoir for passing rinsing liquid therethrough for cleaning purposes.

9. The apparatus of claim 1 wherein said liquid transfer station further includes a withdrawal pump for withdrawing waste liquid from one or more receptacles of said package and delivering said waste liquid to a waste collection area.

10. The apparatus of claim 1 which further includes a device for automatically obtaining test-related information from the reagent package prior to the transfer of liquids with respect to the receptacles thereof.

11. The apparatus of claim 10 wherein said device is a bar-code scanner for electro-optically reading a bar-code label on a reagent package, said apparatus further including means for processing said label information obtained by the bar-code scanner for performing the analysis of the sample.

12. The apparatus of claim 11 wherein said processing means includes means for electro-optically reading a set marker associated with said rack for identifying the set according to which the reagent packages are positioned in said rack and for performing the analyses in accordance with said set.

13. The apparatus of claim 12 wherein said processing means controls the order that individual reagent packages, grouped by set, are transported by said shuttle system from the rack to the liquid transfer station.

14. The apparatus of claim 13 wherein said processing means is operative to read more than one set marker on a given rack and to perform different analyses according to the different sets.

15. The apparatus of claim 1 wherein said shuttle system includes a first drive mechanism to incrementally step said rack positioned in said introduction station so that any one of said reagent packages is positionable adjacent said liquid transfer station.

16. The apparatus of claim 15 wherein said drive mechanism is operative to step said rack translationally, in either direction, across the entrance to said liquid transfer station, said shuttle system further including a second drive mechanism operative in a direction substantially perpendicular to said first drive mechanism for removing one reagent package at a time from said rack and transporting said package to said liquid transfer station and said incubation storage area, and in the reverse direction back to said rack.

17. The apparatus of claim 16 wherein said second drive mechanism and said liquid transfer station cooperatively include means for maintaining the reagent package in substantially movement-free position when such package is in said liquid transfer station.

18. The apparatus of claim 17 wherein said maintaining means includes a spring-biased wall engageable with said reagent package for maintaining the position of said package in the liquid transfer station.

19. The apparatus of claim 1 wherein the incubation storage area includes a rotatable carousel having a plurality of radially extending slots for the receipt of said reagent packages transported thereto by said shuttle system.

20. The apparatus of claim 19 wherein said carousel is rotatable in clockwise and counterclockwise directions to either accept from or deliver to said shuttle system the reagent packages.

21. The apparatus of claim 19 wherein rotation of said carousel for accepting or delivering reagent packages is regulated by control means.

22. The apparatus of claim 19 wherein said carousel is in a temperature-controlled environment for incubating the reagent packages.

23. The apparatus of claim 22 wherein said environment is an air bath maintainable at a relatively constant temperature.

24. The apparatus of claim 1 which further includes means for positioning individual reagent packages adjacent to said detector so that one such package at a time may be analyzed thereby.

25. The apparatus of claim 24 wherein said detector includes a light source for directing light energy into one of the receptacles of the reagent package which contains the reaction mixture for analysis.

26. The apparatus of claim 25 wherein said detector includes at least one means for receiving light associated with the receptacle into which light energy is directed and for associating said received light with a characteristic of the sample under analysis.

27. The apparatus of claim 1 which further includes assay formatting means associated with said liquid transfer station for regulating the actions of said liquid transfer station for transferring liquid into, out of or among the receptacles of a reagent package.

28. The apparatus of claim 27 wherein said formatting means includes one or more control mechanisms for recognizing the type of liquids contained in each package, the location of such liquids, the volumes of liquid in the receptacles and the transfer requirements into, out of or among the receptacles.

29. The apparatus of claim 28 wherein said control mechanisms include a computer program into which information regarding said liquids is storable, retrievable, usable or changeable for analysis of the sample.

30. The apparatus of claim 1 which further includes scheduling means for determining the sequence that reagent packages pass, in any order and in any direction, between the rack, the liquid transfer station, the incubation storage area and the detector.

31. The apparatus of claim 30 wherein said scheduling means includes means for determining when reagent packages are introduced into the apparatus, for recalling information about reagent packages previously introduced into the apparatus and for scheduling a sequence for processing the identified reagent packages according to pre-programmed priorities.

32. The apparatus of claim 31 wherein said scheduling means is pre-programmed to schedule processing of reagent packages in the following order or priority:
  a. reagent packages on which processing has started to be continued;
  b. specially designated reagent packages for immediate processing;
  c. reagent packages which have been in the apparatus longer than a pre-determined time and on which processing has not begun; and
  d. reagent packages recently introduced into the apparatus.

33. The apparatus of claim 32 wherein reagent packages of more complexity within each listed scheduling category are scheduled with a higher priority, complexity being determined by the number of processing steps to process any reagent package.

34. The apparatus of claim 33 wherein said scheduling means accords a higher priority to a reagent package, within each listed scheduling category, which has a shorter incubation period than other packages in the same scheduling group.

35. The apparatus of claim 34 wherein said scheduling means includes a computer program into which information regarding said scheduling is storable, retrievable, usable or changeable for analysis of the samples.

36. An automated analytical apparatus comprising:
  means for receiving a plurality of reagent packages each having a plurality of receptacles at least one of which includes a sample liquid, and at least one of which includes a liquid reagent for forming a reaction mixture with said sample liquid, said means for receiving including a platform for holding an elongate rack having a plurality of slots along a longitudinal axis thereof, said reagent packages being removably positioned in said slots;
  means for transferring liquid contained in one or more receptacles of a reagent package to a different receptacle thereof, whereby a reaction mixture may be formed;
  detector means for detecting a characteristic of the sample by analyzing the reaction mixture contained in one of the receptacles of a package;
  means for storing a plurality of reagent packages; and
  means for transporting individual reagent packages in any order and in any direction between the means for receiving, the means for transferring liquid, the detector means and the means for storing.

37. An automated apparatus for analysis of samples comprising:
  an introduction station for the placement of a rack containing a plurality of reagent packages, each package having a plurality of receptacles at least one of which includes a sample liquid, and at least one of which includes a liquid reagent for forming a reaction mixture with said sample liquid;
  a liquid transfer station including a dual action pump for aspirating liquid from one or more receptacles of a single reagent package and for delivering said aspirated liquid into one or more receptacles of said reagent package, said transfer of liquids including the mixing of said sample liquid and said liquid reagent to form a reaction mixture in at least one of the receptacles of said package;
  a device for automatically obtaining test related information from the reagent package prior to the transfer of liquids with respect to the receptacles thereof;
  means for processing said obtained information for performing the analysis of the reaction mixture, said processing means including means for reading a set marker associated with said rack for identifying the set according to which the reagent packages are positioned in said rack and for performing the analyses in accordance with said set, and further including assay formatting means associated with said liquid transfer station for regulating the actions of said liquid transfer station for transferring liquid into, out of or among the receptacles of the reagent package;
  an incubation storage area including a rotatable carousel having a plurality of radially extending slots for the receipt of said reagent packages transported thereto, said carousel being in a temperature-controlled environment for incubating the reagent packages;
  a shuttle system for moving said rack so that each package therein is positionable adjacent said liquid transfer station and for removing one of said packages at a time from the rack and moving it into said transfer station and into said carousel, said shuttle system being further operative to move individual packages from the carousel into said transfer station and into said rack in the introduction station;
  a detector including a light source for directing light energy into one of the receptacles of the reagent package which contains the reaction mixture for analysis and further including means for receiving light associated with the receptacle into which light energy is directed and for associating said received light with a characteristic of the sample under analysis; and
  scheduling means for determining the sequence that reagent packages pass, in any order and in any direction, between the rack, the liquid transfer station, the carousel and the detector.

* * * * *